United States Patent [19]

Juaire

[11] 4,405,234
[45] Sep. 20, 1983

[54] RADIATION DETECTION APPARATUS HAVING REFRACTIVE LIGHT CHECKING FEATURE

[75] Inventor: Michael P. Juaire, Chaska, Minn.

[73] Assignee: Detector Electronics Corp., Minneapolis, Minn.

[21] Appl. No.: 289,813

[22] Filed: Aug. 3, 1981

[51] Int. Cl.³ .......................................... G01N 21/88
[52] U.S. Cl. ................................ 356/239; 250/252.1; 250/372
[58] Field of Search ............... 340/578, 600; 250/339, 250/372, 252.1, 554, 356; 356/237, 239

[56] References Cited

U.S. PATENT DOCUMENTS 3,540,025  11/1970  Levin et al. ................. 356/136
3,723,746  3/1973   Lawson et al. ............. 250/554
3,952,196  4/1976   Larsen ......................... 250/372

Primary Examiner—Vincent P. McGraw

[57] ABSTRACT

Apparatus for detecting hazardous radiation with a light sensitive radiation receiving tube enclosed in a housing behind a transparent window, and including an auxiliary internal light source positioned for transmitting light rays into the window and reflecting a portion thereof from the front interface surface of the window back to an internal mirror and to the radiation detection tube for self checking purposes.

19 Claims, 4 Drawing Figures

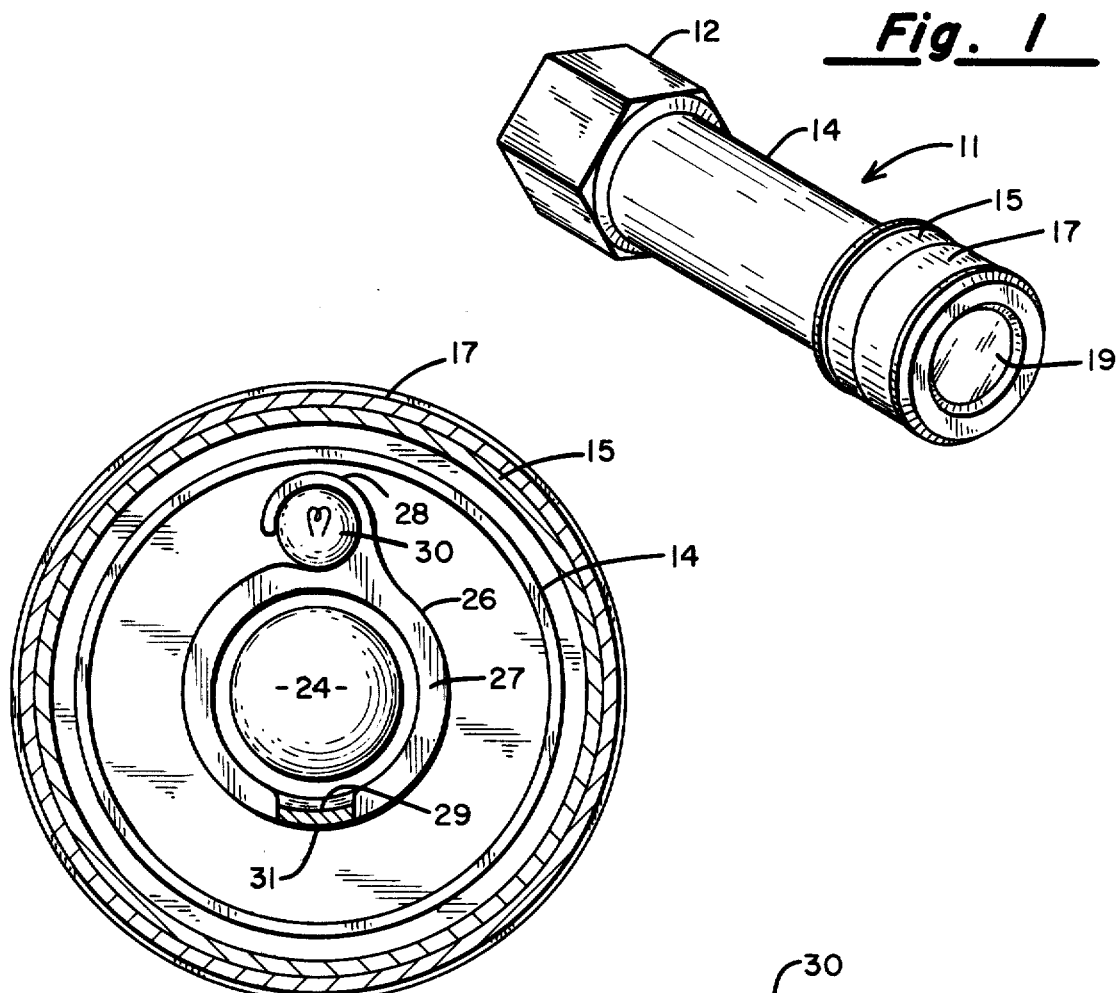
Fig. 1
Fig. 3
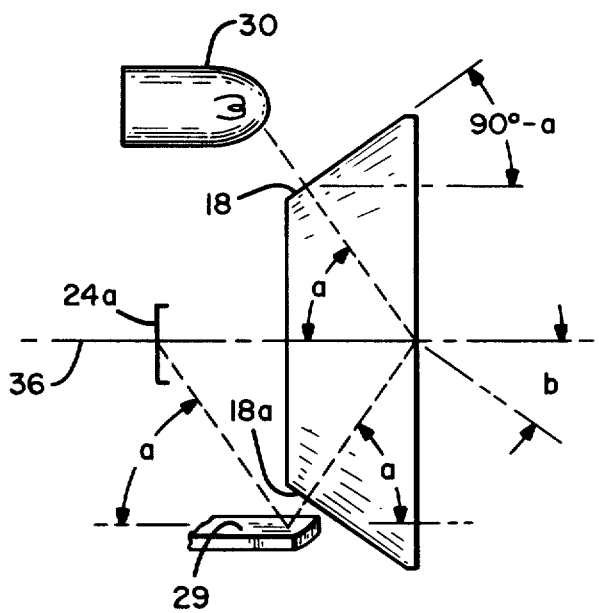
Fig. 4

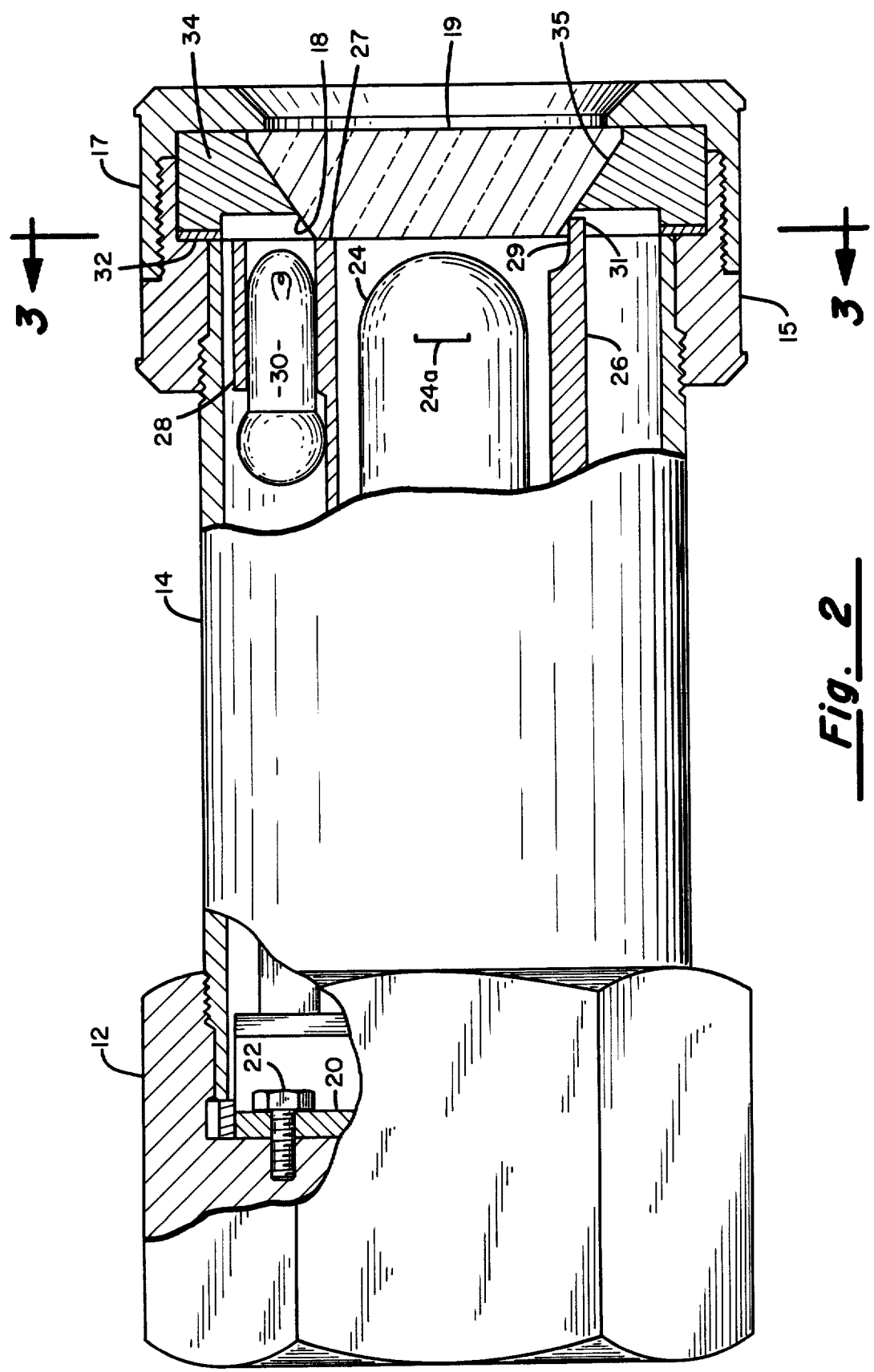

RADIATION DETECTION APPARATUS HAVING REFRACTIVE LIGHT CHECKING FEATURE

BACKGROUND OF THE INVENTION

This invention relates to a radiation detection apparatus, and particularly to a radiation detection apparatus having an auxiliary internal light source and light transmission paths for self checking the operation of the radiation detector as well as the relative contamination of the transparent window in the housing of the detection apparatus.

U.S. Pat. No. 3,952,196, issued Apr. 20, 1976, and owned by the assignee of the present invention, discloses a device for determining whether the optical surfaces through which radiation must travel from a hazardous area of radiation to a radiation detector are free from radiation absorbing material or radiation blocking material. The device disclosed in the patent includes an enclosure for commonly housing both the auxiliary light source and the radiation detector tube, while isolating the same from each other, preventing radiation transmission within the housing from the light source to the detector. The patent also discloses a radiation path from the light source outwardly from the housing to a reflective surface or surfaces external of the housing, which surfaces reflect at least some of the radiation back to the detector through the same optical surfaces that other external radiation passes. The patent contemplates external reflective surfaces which either form a part of the outside housing structure, or are remotely located therefrom.

The prior art invention provides a self checking feature for radiation detection devices in many applications, but also suffers disadvantages which limit its usefulness in certain other applications. For example, when the radiation detection apparatus is placed in a corrosive atmosphere, such as an atmosphere laden with chemically corrosive vapors, the external reflective surfaces tend to suffer from the corrosive or contaminating effects and degrade their ability for efficient light reflectivity. The degradation of the reflecting surfaces causes false fault indications and/or indication that the radiation detection device is inoperative when in fact it continues to function normally in all respects except its self-checking features.

It is therefore desirable to provide a radiation detection apparatus having a self-contained check circuit for periodically testing the light receiving characteristics of the radiation detection tube, and the light transmissive characteristics of the transparent window of the device, without generating false fault indications in situations where the radiation detection device is functioning normally.

It is also desirable to provide a radiation detection device having self-checking features, wherein the device and its self-checking features are all protected from hostile environments.

SUMMARY OF THE INVENTION

The invention includes an enclosed housing having a light transparent window at one end thereof. A radiation detection tube is enclosed within the housing, and an auxiliary light source is enclosed within the housing in optical isolation with respect to the radiation detection tube. The transparent window has a beveled edge surface and the auxiliary light source is positioned so as to radiate light through the beveled edge, a portion of which light reflects backward from the interface surface of the front of the transparent window and back through the diametrically opposite beveled edge of the transparent window. A mirrored surface is positioned to collect and reflect the light so received, and to direct the light radiation to the detection tube.

It is a principal object of the present invention to provide a radiation detection apparatus having enclosed and protected self checking elements.

It is another object of the present invention to provide a radiation detection apparatus having a transparent window for viewing a hazardous radiation area, with means for checking the relative transparency of the window.

These and other objects and advantages of the invention will become apparent from the following specifications and drawings.

BRIEF DESCRIPTION OF THE DRAWINGS

FIG. 1 shows the invention in perspective view; and

FIG. 2 shows the invention in side view, in partial cross section; and

FIG. 3 shows a view taken along the lines 3—3 of FIG. 2; and

FIG. 4 shows a symbolic diagram of the checking features of the invention.

DESCRIPTION OF THE PREFERRED EMBODIMENT

Referring first to FIG. 1, radiation detection apparatus 11 is shown in perspective view. A base 12 is adapted for external attachment to a support mechanism, and for securing to housing member 14. A sleeve 15 is threadably attached over the end of housing member 14. A cap 17 is threadably attached to sleeve 15, and clamps window 19 against the end of shield manner 26.

FIG. 2 shows the invention in side view, and in partial cross-section. Housing member 14 is threadably attached into base 12. Radiation detection tube 24 is a Geiger-Muller type radiation detector tube, sensitive to radiation in the wavelength range of 1850-2750 Angstroms (A). This wavelength range is characteristic of radiation from a fire source, which is the wavelength range in which the invention is primarily intended to operate. A cylindrical shield member 26 is attached to plate 20, concentrically surrounding detector tube 24. Shield member 26 has a cylindrical bracket 28 formed as a part thereof, bracket 28 being adapted for holding light source 30. Light source 30 is similar to the light source disclosed in U.S. Pat. No. 3,952,196, generating light radiation in the wavelength range 1850-2750 A. Shield member 26 completely optically isolates light radiation from light source 30 from direct impingement against radiation tube 24.

A sealing member 32 is positioned adjacent the end of housing member 14. A retaining ring 34 is clamped against sealing member 32 by means of threadable end cap 17. Window 19 has a beveled edge surface mated for seating into retaining ring 34.

A segment 18 of the beveled edge surface of window 19 is exposed to radiation from light source 30. Light radiation from light source 30 enters into window 19 through segment 18 and is reflected therein as will be hereinafter described.

FIG. 3 shows a cross-sectional view taken along the lines 3—3 of FIG. 2. Cap 17 is threadably attached to sleeve 15, which itself is threadably attached to housing 14. Detector tube 24 is concentrically positioned within housing 14, and is concentrically positioned relative to shield member 26. Shield member 26 has an arcuate bracket 28 for holding light source 30. Shield member 26 also has an arcuate reflective surface portion 29 diametrically opposite light source 30. Surface 29 is preferably a highly polished mirrored surface having the capability of reflecting most of the light radiation impinging thereon. Mirrored surface 29 is formed along the inside surface of an arcuate tab 31 which projects beyond the end 27 of shield member 26. In the preferred embodiment, tab 31 projects beyond the forward edge 27 of shield member 26, placing it in close adjacent position relative to the beveled edge of window 19.

FIG. 4 shows a symbolic diagram illustrating the geometric relationships important to the present invention. It is generally known in the science of physics and optics that a ray of light undergoes refraction at a surface separating two regions of different indexes of refraction. Snell's law governs the relationship for rays of light intersecting a plane surface interface as follows:

$n \sin i = n' \sin i'$ where $n$ = index of refraction of first material;
$i$ = angle of incidence of light against first material surface;
$n'$ = index of refraction of second material;
$i'$ = angle of light refraction from surface of second material.

The above equation makes it possible to determine the angle of refraction of light rays from a plane interface if the angle of incidence is known, and the indexes of refraction of the two materials at the interface are also known. When the angle of refraction equals 90°, the angle of incidence is equal to the "critical angle". No light will be refracted at the interface if, for a given combination of two materials forming the interface, the angle of incidence is made greater than the "critical angle". This critical angle depends upon the indexes of refraction of the materials, as well as the angle of incidence of the impinging light. For example, for a planar interface between glass ($n = 1.5$) and air ($n = 1.0$) the critical angle is approximately 42 degrees. For any angle of incidence greater than the critical angle no light will be refracted and all light will be reflected from the surface interface. In the preferred embodiment of the present invention window 19 is constructed of an ultraviolet transmitting material such as fused silica, which has an index of refraction very close to glass (1.48–1.57) thus, the critical angle for a silica/air planar interface is approximately the same as a glass/air interface. Since it is important to the present invention to choose an angle of incidence "a" of light rays to the planar surface interface greater than the critical angle, the angle "a" is selected to be 54°. Light rays impinging upon segment 18 of window 19 are normal to segment 18. By selecting the bevel angle of segment 18 to be (90°—a) or 36°, light rays impinging on the planar interface between the front surface of window 19 and air will be substantially totally reflected therefrom at the same angle. These light rays will impinge segment 18a, diametrically opposite of segment 18, at a normal angle, and will be directed onto mirrored surface 29. Mirrored surface 29 is aligned parallel with the axis 36 of window 19 and detector tube 24. Light rays are therefore reflected therefrom at the angle a towards detector tube 24. Detector tube 24 is positioned along axis 36 so as to place its photo receptive element 24a at the focal point for light rays being reflected from mirrored surface 29.

This permits detector tube 24 to receive the maximum amount of light transmitted from light source 30 and reflected from the various surfaces described herein.

In operation, detector tube 24 receives light radiation through window 19 from radiation sources lying in the field of view. Since the apparatus in practice is placed in locations where it may have a full field of view of potentially hazardous radiation sources such as fires, detector tube 24 is in a position to sense this radiation as soon as it is generated. In order that the function and operation of all elements associated with the apparatus may be periodically tested, the light source 30 is periodically illuminated by means of external electrical controls, and the signal received by circuits connected to detector tube 24 are monitored to insure that all components are operating as expected.

It has been established through experimentation that the amount of radiation loss through window 19 as a result of surface contamination is directly proportional to the amount of light lost through refraction effects at the interface surface. Therefore, the degradation of light from light source 30 to detector tube 24 from surface contamination is roughly the same as the degradation of radiation received by detector tube 24 through window 19 from external radiation sources. In the event the front surface of window 19 becomes covered by contaminants such as oil or other moist contaminants, such contaminants will change the index of refraction at the interface surface with window 19. When the index of refraction becomes thus changed, a new "critical angle" is established for light rays impinging upon the interface at the angle "a". Since the index of refraction of all known and likely contaminants is considerably greater than the index of refraction of air, the new "critical angle" thus established will be greater than the angle "a" which as been set at 54°. This will cause a portion of the light emitted from light source 30 to become refracted through the interface surface at a refraction angle "b" and therefore not reflected back toward mirrored surface 29. This will result in a net reduction in light intensity being received by detector tube element 24a, which will be recognized as a reduction in electrical signal in the receiving circuits connected to detector tube 24. Such circuits are designed to indicate an alarm condition when this reduction in signal level is detected, and the apparatus will automatically recognize its own impaired ability for radiation detection.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. A radiation detection apparatus having facility for self checking of optical surface contamination, comprising:

(a) a housing having an opening at one end thereof;
(b) a radiation-sensitive receiving device in said housing;
(c) a light transmissive window mounted in said housing opening, said window having flat parallel surfaces orthogonal to said radiation sensitive receiving device and a beveled edge surface facing toward the interior of said housing;

(d) an optical shielding member about said receiving device and having an opening facing said window, said shielding member opening further comprising a first edge portion contacting said window interior flat surface and a second edge portion terminating in the region of said beveled edge surface, said second edge portion having a reflective surface area facing said beveled edge surface;

(e) a light source mounted in said housing outside said optical shielding member, and positioned relative to said beveled edge so as to cause light from said light source to travel through said beveled edge and be refracted from said window outer parallel surface to said optical shielding member second edge portion reflective surface, and reflected therefrom to said radiation-sensitive receiving device.

2. The apparatus of claim 1, wherein said housing is a cylindrical member about an axis.

3. The apparatus of claim 2, wherein said radiation-sensitive receiving device is mounted along said axis.

4. The apparatus of claim 3, wherein said optical shielding member is concentrically mounted about said receiving device.

5. The apparatus of claim 4, wherein the angle of said window beveled edge surface relative to said axis is approximately 36°.

6. The apparatus of claim 4, wherein said light reflecting means is formed on a tab extending axially from a portion of said optical shielding member.

7. The apparatus of claim 6, wherein said window is mounted normal to said axis.

8. The apparatus of claim 7, wherein said tab is positioned diametrically opposite said light source.

9. The apparatus of claim 8, wherein said window is constructed of fused silica.

10. The apparatus of claim 9, further comprising a bracket on said shielding member adapted for holding said light source.

11. In a radiation detection apparatus of the type having a radiation-sensitive element enclosed in a housing having a radiation-transparent window at the receiving end thereof, the improvement in self-checking features comprising (a) a radiation source in said housing and a radiation shield in said housing between said radiation source and said radiation-sensitive element; said radiation shield having a first edge portion in radiation-shielding contact against said window and interposed between said radiation source and said radiation-sensitive element, and a second edge portion displaced from said window at a position where said radiation-sensitive element is between said second edge portion and said radiation source, said second edge portion having a reflective surface area facing toward said radiation-sensitive element;

(b) a beveled edge on said radiation-transparent window facing said radiation source, and also facing said second edge portion; whereby a radiation path exists from said radiation source through said facing beveled window edge, through said window to said reflecting surface from said adjacent beveled edge, and to said radiation-sensitive element.

12. The improvement of claim 11, wherein said housing is a cylindrical member about an axis and said window is normal to said axis.

13. The improvement of claim 12, wherein said radiation-sensitive element is positioned on said axis.

14. The improvement of claim 13, wherein said radiation shield is positioned concentric about said radiation-sensitive element.

15. The improvement of claim 14, wherein said radiation-reflecting surface is formed on a tab extending axially from said radiation shield.

16. The improvement of claim 15, wherein said window is circular and said edge bevel extends around the circumference of said window.

17. The improvement of claim 16, wherein said tab is positioned diametrically opposite said radiation source.

18. The improvement of claim 17, wherein said window is constructed of fused silica.

19. The improvement of claim 18, wherein said edge bevel is approximately 36° relative to said housing axis.

* * * * *